(12) United States Patent
Brady

(10) Patent No.: US 8,328,842 B2
(45) Date of Patent: Dec. 11, 2012

(54) FILTER ELEMENT WITH RETRACTABLE GUIDEWIRE TIP

(75) Inventor: Eamon Brady, Elphin (IE)

(73) Assignee: Salviac Limited, Dublin (IE)

( * ) Notice: Subject to any disclaimer, the term of this patent is extended or adjusted under 35 U.S.C. 154(b) by 0 days.

(21) Appl. No.: 13/022,040

(22) Filed: Feb. 7, 2011

(65) Prior Publication Data

US 2011/0125182 A1 May 26, 2011

Related U.S. Application Data

(60) Continuation of application No. 12/339,375, filed on Dec. 19, 2008, now Pat. No. 7,901,427, which is a division of application No. 10/189,375, filed on Jul. 3, 2002, now Pat. No. 7,491,216, which is a continuation of application No. 09/986,060, filed on Nov. 7, 2001, now abandoned, which is a continuation of application No. PCT/IE00/00057, filed on May 8, 2000, and a continuation-in-part of application No. 09/188,472, filed on Nov. 9, 1998, now Pat. No. 6,336,934.

(30) Foreign Application Priority Data

Nov. 7, 1997 (IE) .......................................... 970789
Apr. 8, 1998 (IE) .......................................... 980267
May 7, 1999 (IE) ........................... PCT/IE99/00039

(51) Int. Cl.
*A61M 29/00* (2006.01)
*A61M 31/00* (2006.01)

(52) U.S. Cl. ...................... 606/200; 604/500; 604/96.01

(58) Field of Classification Search .................. 606/191, 606/198, 200; 600/433–435, 585; 604/93.01, 604/96.01, 264, 500, 523, 528
See application file for complete search history.

(56) References Cited

U.S. PATENT DOCUMENTS

| | | |
|---|---|---|
| 2,854,983 A | 10/1958 | Baskin |
| 2,943,626 A | 7/1960 | Dormia |
| 3,334,629 A | 9/1967 | Cohn |

(Continued)

FOREIGN PATENT DOCUMENTS

DE 3706077 6/1988

(Continued)

OTHER PUBLICATIONS

Beck et al., "Dilatation of the Carotid Artery by a Temporary Carotid Filter", Edizioni Oplitai—Via dei Foscari N° 7 -00162 Roma, Spediz, In Abb. Postale Gruppo IV—70%—Anno II N. 6 Nov.-Dec. 1989 L. 800.

(Continued)

*Primary Examiner* — Victoria P Shumate

(74) *Attorney, Agent, or Firm* — Sughrue Mion, PLLC; Jonathan Feuchtwang

(57) ABSTRACT

A medical guidewire assembly comprises a guidewire having a flexible tip. A medical device such as a collapsible filter for use as an embolic protection device is mounted on the guidewire. The filter is advanced through a body lumen with the guidewire tip extending distally. A variable thickness guidewire (having a recess or thinner segment between thicker segments) can be employed. At a first location the filter is advanced relative to the tip to a location which is distally advanced from the first location. Placement of the filter in an optimal distal location is thereby achieved.

21 Claims, 9 Drawing Sheets

U.S. PATENT DOCUMENTS

| | | | |
|---|---|---|---|
| 3,435,824 | A | 4/1969 | Gamponia |
| 3,540,431 | A | 11/1970 | Mebin-Uddin |
| 3,692,029 | A | 9/1972 | Adair |
| 3,730,185 | A | 5/1973 | Cook et al. |
| 3,952,747 | A | 4/1976 | Kimmell, Jr. |
| 4,295,464 | A | 10/1981 | Shihata |
| 4,404,971 | A | 9/1983 | LeVeen et al. |
| 4,423,725 | A | 1/1984 | Baran et al. |
| 4,425,908 | A | 1/1984 | Simon |
| 4,425,909 | A | 1/1984 | Rieser |
| 4,445,892 | A | 5/1984 | Hussein et al. |
| 4,493,711 | A | 1/1985 | Chin et al. |
| 4,512,762 | A | 4/1985 | Spears |
| 4,585,000 | A | 4/1986 | Hershenson |
| 4,586,919 | A | 5/1986 | Taheri |
| 4,610,662 | A | 9/1986 | Weikl et al. |
| 4,611,594 | A | 9/1986 | Grayhack et al. |
| 4,619,246 | A | 10/1986 | Molgaard-Nielsen et al. |
| 4,643,184 | A | 2/1987 | Mobin-Uddin |
| 4,650,466 | A | 3/1987 | Luther |
| 4,712,551 | A | 12/1987 | Rayhanabad |
| 4,723,549 | A | 2/1988 | Wholey et al. |
| 4,781,177 | A | 11/1988 | Lebigot |
| 4,790,812 | A | 12/1988 | Hawkins, Jr. et al. |
| 4,794,928 | A | 1/1989 | Kletschka |
| 4,807,626 | A | 2/1989 | McGirr |
| 4,817,600 | A | 4/1989 | Herms et al. |
| 4,832,055 | A | 5/1989 | Palestrant |
| 4,867,156 | A | 9/1989 | Stack et al. |
| 4,873,978 | A | 10/1989 | Ginsburg |
| 4,926,858 | A | 5/1990 | Gifford, III et al. |
| 4,927,426 | A | 5/1990 | Dretler |
| 4,957,501 | A | 9/1990 | Lahille et al. |
| 4,969,891 | A | 11/1990 | Gevertz |
| 4,990,156 | A | 2/1991 | Lefebvre |
| 5,011,488 | A | 4/1991 | Ginsburg |
| 5,026,377 | A | 6/1991 | Burton et al. |
| 5,053,008 | A | 10/1991 | Bajaj |
| 5,092,839 | A | 3/1992 | Kipperman |
| 5,100,423 | A | 3/1992 | Fearnot |
| 5,108,419 | A | 4/1992 | Reger et al. |
| 5,122,125 | A | 6/1992 | Deuss |
| 5,133,733 | A | 7/1992 | Rasmussen et al. |
| 5,171,233 | A | 12/1992 | Amplatz et al. |
| 5,178,158 | A | 1/1993 | De Toledo |
| 5,192,284 | A | 3/1993 | Pleatman |
| 5,192,295 | A * | 3/1993 | Danforth et al. ............... 606/194 |
| 5,254,622 | A | 10/1993 | Nanasawa et al. |
| 5,256,144 | A * | 10/1993 | Kraus et al. ................ 604/96.01 |
| 5,324,304 | A | 6/1994 | Rasmussen |
| 5,329,942 | A | 7/1994 | Gunther et al. |
| 5,336,234 | A | 8/1994 | Vigil et al. |
| 5,354,310 | A | 10/1994 | Garnic et al. |
| 5,370,657 | A | 12/1994 | Irie |
| 5,375,612 | A | 12/1994 | Cottenceau et al. |
| 5,383,887 | A | 1/1995 | Nadal |
| 5,387,219 | A | 2/1995 | Rappe |
| 5,405,329 | A | 4/1995 | Durand |
| 5,421,832 | A | 6/1995 | Lefebvre |
| 5,454,788 | A | 10/1995 | Walker et al. |
| 5,540,707 | A | 7/1996 | Ressemenn et al. |
| 5,549,626 | A | 8/1996 | Miller et al. |
| 5,593,394 | A | 1/1997 | Kanesaka et al. |
| 5,621,065 | A | 4/1997 | Pudleiner et al. |
| 5,658,296 | A | 8/1997 | Bates et al. |
| 5,662,671 | A | 9/1997 | Barbut et al. |
| 5,669,933 | A | 9/1997 | Simon et al. |
| 5,683,451 | A | 11/1997 | Lenker et al. |
| 5,695,519 | A | 12/1997 | Summers et al. |
| 5,709,704 | A | 1/1998 | Nott et al. |
| 5,720,764 | A | 2/1998 | Naderlinger |
| 5,725,519 | A | 3/1998 | Penner et al. |
| 5,766,203 | A | 6/1998 | Imran et al. |
| 5,769,816 | A | 6/1998 | Barbut et al. |
| 5,769,871 | A | 6/1998 | Mers Kelly et al. |
| 5,779,716 | A | 7/1998 | Cano et al. |
| 5,795,322 | A | 8/1998 | Boudewijn |
| 5,800,457 | A | 9/1998 | Gelbfish |
| 5,800,525 | A | 9/1998 | Bachinski et al. |
| 5,810,874 | A | 9/1998 | Lefebvre |
| 5,814,064 | A | 9/1998 | Daniel et al. |
| 5,823,992 | A | 10/1998 | Salmon et al. |
| 5,827,324 | A | 10/1998 | Cassell et al. |
| 5,834,449 | A | 11/1998 | Thompson et al. |
| 5,836,969 | A | 11/1998 | Kim et al. |
| 5,843,167 | A | 12/1998 | Dwyer et al. |
| 5,846,260 | A | 12/1998 | Maahs |
| 5,848,964 | A | 12/1998 | Samuels |
| 5,876,367 | A | 3/1999 | Kaganov et al. |
| 5,879,697 | A | 3/1999 | Ding et al. |
| 5,882,329 | A | 3/1999 | Pattrson et al. |
| 5,895,398 | A | 4/1999 | Wensel et al. |
| 5,895,410 | A | 4/1999 | Forber et al. |
| 5,897,567 | A | 4/1999 | Ressemann et al. |
| 5,902,334 | A | 5/1999 | Dwyer et al. |
| 5,910,154 | A | 6/1999 | Tsugita et al. |
| 5,911,725 | A | 6/1999 | Boury |
| 5,911,734 | A | 6/1999 | Tsugita et al. |
| 5,928,261 | A | 7/1999 | Ruiz |
| 5,935,139 | A | 8/1999 | Bates |
| 5,941,869 | A | 8/1999 | Patterson et al. |
| 5,941,896 | A | 8/1999 | Kerr |
| 5,947,995 | A | 9/1999 | Samuels |
| 5,954,745 | A | 9/1999 | Gertler et al. |
| 5,968,071 | A | 10/1999 | Chevillon |
| 5,976,172 | A | 11/1999 | Homsma et al. |
| 5,984,947 | A | 11/1999 | Smith |
| 5,989,281 | A | 11/1999 | Barbut et al. |
| 5,993,469 | A | 11/1999 | McKenzie et al. |
| 5,997,557 | A | 12/1999 | Barbut et al. |
| 6,001,118 | A | 12/1999 | Daniel et al. |
| 6,007,557 | A | 12/1999 | Ambrisco et al. |
| 6,010,522 | A | 1/2000 | Barbut et al. |
| 6,013,093 | A | 1/2000 | Nott et al. |
| 6,027,509 | A | 2/2000 | Schatz et al. |
| 6,027,520 | A | 2/2000 | Tsugita et al. |
| 6,042,598 | A | 3/2000 | Tsugita et al. |
| 6,051,014 | A | 4/2000 | Jang |
| 6,053,832 | A | 4/2000 | Saito |
| 6,053,932 | A | 4/2000 | Daniel et al. |
| 6,059,814 | A | 5/2000 | Ladd |
| 6,066,149 | A | 5/2000 | Samson et al. |
| 6,068,645 | A | 5/2000 | Tu |
| 6,074,357 | A | 6/2000 | Kaganov et al. |
| 6,083,239 | A | 7/2000 | Addis |
| 6,086,577 | A | 7/2000 | Ken et al. |
| 6,086,605 | A | 7/2000 | Barbut et al. |
| 6,090,097 | A | 7/2000 | Barbut et al. |
| 6,093,173 | A | 7/2000 | Balceta et al. |
| 6,096,027 | A | 8/2000 | Layne |
| 6,096,053 | A | 8/2000 | Bates |
| 6,099,534 | A | 8/2000 | Bates et al. |
| 6,099,549 | A | 8/2000 | Bosma et al. |
| 6,123,715 | A | 9/2000 | Amplatz |
| 6,129,739 | A | 10/2000 | Khosravi |
| 6,132,458 | A | 10/2000 | Staehle et al. |
| 6,142,987 | A | 11/2000 | Tsugita |
| 6,146,370 | A | 11/2000 | Barbut |
| 6,146,404 | A | 11/2000 | Kim et al. |
| 6,152,946 | A | 11/2000 | Broome et al. |
| 6,165,199 | A | 12/2000 | Barbut |
| 6,165,200 | A | 12/2000 | Tsugita et al. |
| 6,168,579 | B1 | 1/2001 | Tsugita |
| 6,168,604 | B1 | 1/2001 | Cano |
| 6,171,327 | B1 | 1/2001 | Daniel et al. |
| 6,171,328 | B1 | 1/2001 | Addis |
| 6,176,849 | B1 | 1/2001 | Yang et al. |
| 6,179,859 | B1 | 1/2001 | Bates et al. |
| 6,179,861 | B1 | 1/2001 | Khosravi et al. |
| 6,203,561 | B1 | 3/2001 | Ramee et al. |
| 6,206,868 | B1 | 3/2001 | Parodi |
| 6,214,026 | B1 | 4/2001 | Lepak et al. |
| 6,238,412 | B1 | 5/2001 | Dubrul et al. |
| 6,241,703 | B1 * | 6/2001 | Levin et al. ..................... 604/22 |
| 6,241,746 | B1 | 6/2001 | Bosma et al. |
| 6,245,012 | B1 | 6/2001 | Kleshinski |
| 6,245,087 | B1 | 6/2001 | Addis |

| Patent No. | Date | Inventor |
|---|---|---|
| 6,245,088 B1 | 6/2001 | Lowery |
| 6,245,089 B1 | 6/2001 | Daniel et al. |
| 6,251,122 B1 | 6/2001 | Tsukernik |
| 6,254,563 B1 | 7/2001 | Macoviak et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,371,935 B1 | 4/2002 | Macoviak et al. |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,395,017 B1 | 5/2002 | Dwyer et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,425,909 B1 | 7/2002 | Dieck et al. |
| 6,428,489 B1 * | 8/2002 | Jacobsen et al. ............. 600/585 |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,979 B1 | 9/2002 | Stalker et al. |
| 6,447,530 B1 | 9/2002 | Ostrovsky et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,494,895 B2 | 12/2002 | Addis |
| 6,506,203 B1 | 1/2003 | Boyle et al. |
| 6,506,205 B2 | 1/2003 | Goldberg et al. |
| 6,511,492 B1 | 1/2003 | Rosenbluth |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Petersen |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,760 B1 | 4/2003 | Samson et al. |
| 6,551,341 B2 | 4/2003 | Boylan et al. |
| 6,551,342 B1 | 4/2003 | Shen et al. |
| 6,558,405 B1 | 5/2003 | McInnes |
| 6,562,058 B2 | 5/2003 | Seguin |
| 6,565,591 B2 | 5/2003 | Brady et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,602,269 B2 | 8/2003 | Wallace et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,605,111 B2 | 8/2003 | Bose et al. |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,632,236 B2 | 10/2003 | Hogendijk |
| 6,632,241 B1 | 10/2003 | Hancock et al. |
| 6,635,070 B2 | 10/2003 | Leeflang et al. |
| 6,638,294 B1 | 10/2003 | Palmer |
| 6,645,220 B1 | 11/2003 | Huter et al. |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,660,021 B1 | 12/2003 | Palmer et al. |
| 6,663,650 B2 | 12/2003 | Sepetka et al. |
| 6,663,651 B2 | 12/2003 | Krolike et al. |
| 6,663,652 B2 | 12/2003 | Daniel et al. |
| 6,666,882 B1 | 12/2003 | Bose et al. |
| 6,669,721 B1 | 12/2003 | Bose et al. |
| 6,682,812 B2 | 1/2004 | Scheckenbach et al. |
| 6,695,813 B1 | 2/2004 | Boyle et al. |
| 6,726,701 B2 | 4/2004 | Gilson et al. |
| 6,726,703 B2 | 4/2004 | Broome et al. |
| 6,752,819 B1 | 6/2004 | Brady et al. |
| 6,773,448 B2 | 8/2004 | Kusleika et al. |
| 6,840,950 B2 | 1/2005 | Stanford et al. |
| 6,872,216 B2 | 3/2005 | Daniel et al. |
| 6,887,256 B2 | 5/2005 | Gilson et al. |
| 6,963,760 B2 | 11/2005 | Piwowarski |
| 6,964,670 B1 | 11/2005 | Shah et al. |
| 7,131,986 B2 | 11/2006 | Sirhan et al. |
| 7,172,614 B2 | 2/2007 | Boyle et al. |
| 7,491,215 B2 | 2/2009 | Vale et al. |
| 2001/0000799 A1 | 5/2001 | Wessman et al. |
| 2001/0001315 A1 | 5/2001 | Bates et al. |
| 2001/0007947 A1 | 7/2001 | Kanesaka |
| 2001/0012951 A1 | 8/2001 | Bates et al. |
| 2001/0020175 A1 | 9/2001 | Yassour et al. |
| 2001/0025187 A1 | 9/2001 | Okada |
| 2001/0031982 A1 | 10/2001 | Peterson et al. |
| 2001/0039431 A1 | 11/2001 | De Vries et al. |
| 2001/0041908 A1 | 11/2001 | Levinson et al. |
| 2001/0044632 A1 | 11/2001 | Daniel et al. |

| Publication No. | Date | Inventors |
|---|---|---|
| 2002/0002384 A1 | 1/2002 | Gilson et al. |
| 2002/0004667 A1 | 1/2002 | Adams et al. |
| 2002/0022858 A1 | 2/2002 | Demond et al. |
| 2002/0022860 A1 | 2/2002 | Borillo et al. |
| 2002/0026211 A1 | 2/2002 | Khosravi et al. |
| 2002/0026213 A1 | 2/2002 | Gilson et al. |
| 2002/0032460 A1 | 3/2002 | Kusleika et al. |
| 2002/0045916 A1 | 4/2002 | Gray et al. |
| 2002/0045918 A1 | 4/2002 | Suon et al. |
| 2002/0049467 A1 | 4/2002 | Gilson et al. |
| 2002/0049468 A1 | 4/2002 | Streeter et al. |
| 2002/0052626 A1 | 5/2002 | Gilson et al. |
| 2002/0052638 A1 | 5/2002 | Zadno-Azizi |
| 2002/0055747 A1 | 5/2002 | Cano et al. |
| 2002/0055767 A1 | 5/2002 | Forde et al. |
| 2002/0058911 A1 | 5/2002 | Gilson et al. |
| 2002/0058963 A1 | 5/2002 | Vale et al. |
| 2002/0062133 A1 | 5/2002 | Gilson et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072730 A1 | 6/2002 | McGill et al. |
| 2002/0072765 A1 | 6/2002 | Mazzocchi et al. |
| 2002/0082525 A1 | 6/2002 | Oslund et al. |
| 2002/0082639 A1 | 6/2002 | Broome et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0115942 A1 | 8/2002 | Stanford et al. |
| 2002/0120286 A1 | 8/2002 | DoBrava et al. |
| 2002/0120287 A1 | 8/2002 | Huter |
| 2002/0121472 A1 | 9/2002 | Garner et al. |
| 2002/0123720 A1 | 9/2002 | Kuleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165576 A1 | 11/2002 | Boyle et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kleschka et al. |
| 2002/0183873 A1 | 12/2002 | Shadduck |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady et al. |
| 2003/0040772 A1 | 2/2003 | Hyodoh et al. |
| 2003/0042186 A1 | 3/2003 | Boyle et al. |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0093106 A1 | 5/2003 | Brady et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0109824 A1 | 6/2003 | Anderson et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0125764 A1 | 7/2003 | Brady et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144670 A1 | 7/2003 | Pavcnik et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153942 A1 | 8/2003 | Wang et al. |
| 2003/0153943 A1 | 8/2003 | Michael et al. |
| 2003/0158574 A1 | 8/2003 | Esch et al. |
| 2003/0163064 A1 | 8/2003 | Vrba et al. |
| 2003/0171770 A1 | 9/2003 | Kusleika et al. |
| 2003/0171771 A1 | 9/2003 | Anderson et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191493 A1 | 10/2003 | Epstein et al. |
| 2003/0195555 A1 | 10/2003 | Khairkhahan et al. |
| 2003/0199819 A1 | 10/2003 | Beck |
| 2003/0204168 A1 | 10/2003 | Bosma et al. |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0212361 A1 | 11/2003 | Boyle et al. |
| 2003/0212429 A1 | 11/2003 | Keegan et al. |
| 2003/0212431 A1 | 11/2003 | Brady et al. |
| 2003/0212434 A1 | 11/2003 | Thielen |
| 2003/0216774 A1 | 11/2003 | Larson |
| 2003/0220665 A1 | 11/2003 | Eskuri et al. |

| | | | | | |
|---|---|---|---|---|---|
| 2003/0225418 A1 | 12/2003 | Esksuri et al. | WO | 00/44428 | 8/2000 |
| 2003/0229295 A1 | 12/2003 | Houde et al. | WO | 00/49970 | 8/2000 |
| 2003/0229374 A1 | 12/2003 | Brady et al. | WO | 00/56390 | 9/2000 |
| 2003/0233117 A1 | 12/2003 | Adams et al. | WO | 00/66031 | 11/2000 |
| 2004/0010282 A1 | 1/2004 | Kusleika | WO | 00/67664 | 11/2000 |
| 2004/0204737 A1 | 10/2004 | Boismler et al. | WO | 00/67665 | 11/2000 |
| 2006/0030878 A1 | 2/2006 | Anderson et al. | WO | 00/67666 | 11/2000 |
| 2006/0161198 A1 | 7/2006 | Sakai et al. | WO | 00/67667 | 11/2000 |
| 2007/0027522 A1 | 2/2007 | Chang et al. | WO | 00/67668 | 11/2000 |
| 2007/0135833 A1 | 6/2007 | Talpade et al. | WO | 00/67669 | 11/2000 |

FOREIGN PATENT DOCUMENTS

| | | | | | |
|---|---|---|---|---|---|
| EP | 0256683 | 2/1988 | WO | 00/67670 | 11/2000 |
| EP | 0461375 | 4/1991 | WO | 00/67671 | 11/2000 |
| EP | 0533511 | 3/1993 | WO | 00/67829 | 11/2000 |
| EP | 0596172 | 11/1994 | WO | 00/76390 | 12/2000 |
| EP | 0655228 | 5/1995 | WO | 01/00084 | 1/2001 |
| EP | 0743046 | 11/1996 | WO | 01/00087 | 1/2001 |
| EP | 0759287 | 2/1997 | WO | 01/15329 | 1/2001 |
| EP | 0791340 | 8/1997 | WO | 01/08595 | 2/2001 |
| EP | 0827756 | 3/1998 | WO | 01/08596 | 2/2001 |
| EP | 1123688 | 8/2001 | WO | 01/08742 | 2/2001 |
| EP | 1127556 | 8/2001 | WO | 01/08743 | 2/2001 |
| EP | 1149566 | 10/2001 | WO | 01/10343 | 2/2001 |
| EP | 1172073 | 1/2002 | WO | 01/12081 | 2/2001 |
| EP | 1181900 | 2/2002 | WO | 01/15629 | 3/2001 |
| EP | 1676545 | 7/2006 | WO | 01/15630 | 3/2001 |
| FR | 2580504 | 10/1986 | WO | 01/21077 | 3/2001 |
| FR | 2616666 | 12/1988 | WO | 01/21100 | 3/2001 |
| FR | 2768326 | 3/1999 | WO | 01/35857 | 5/2001 |
| GB | 2020557 | 11/1979 | WO | 01/35858 | 5/2001 |
| GB | 2200848 | 8/1988 | WO | 01/43662 | 6/2001 |
| WO | 88/09683 | 12/1988 | WO | 01/45590 | 6/2001 |
| WO | 89/07422 | 8/1989 | WO | 01/45591 | 6/2001 |
| WO | 94/24946 | 11/1994 | WO | 01/45592 | 6/2001 |
| WO | 95/34254 | 12/1995 | WO | 01/49208 | 7/2001 |
| WO | 95/34339 | 12/1995 | WO | 01/49209 | 7/2001 |
| WO | 96/01591 | 1/1996 | WO | 01/49215 | 7/2001 |
| WO | 96/39998 | 12/1996 | WO | 01/50982 | 7/2001 |
| WO | 97/03810 | 2/1997 | WO | 01/52768 | 7/2001 |
| WO | 97/17021 | 5/1997 | WO | 01/72205 | 10/2001 |
| WO | 97/17100 | 5/1997 | WO | 01/80776 | 11/2001 |
| WO | 97/17914 | 5/1997 | WO | 01/80777 | 11/2001 |
| WO | 97/27808 | 8/1997 | WO | 01/82830 | 11/2001 |
| WO | 97/42879 | 11/1997 | WO | 01/82831 | 11/2001 |
| WO | 98/24377 | 6/1998 | WO | 01/87183 | 11/2001 |
| WO | 98/30265 | 7/1998 | WO | 01/89413 | 11/2001 |
| WO | 98/33443 | 8/1998 | WO | 01/97714 | 12/2001 |
| WO | 98/38920 | 9/1998 | WO | 02/43595 | 6/2002 |
| WO | 98/39053 | 9/1998 | WO | 02/083225 | 10/2002 |
| WO | 98/46297 | 10/1998 | WO | 03/022325 | 3/2003 |
| WO | 98/49952 | 11/1998 | WO | 03/047648 | 6/2003 |
| WO | 98/50103 | 11/1998 | WO | 03/084434 | 10/2003 |
| WO | 98/51237 | 11/1998 | WO | 03/084435 | 10/2003 |
| WO | 99/16382 | 4/1999 | WO | 03/084436 | 10/2003 |
| WO | 99/20335 | 4/1999 | WO | 03/088805 | 10/2003 |
| WO | 99/22673 | 5/1999 | WO | 03/088869 | 10/2003 |
| WO | 99/23976 | 5/1999 | WO | 2004/093738 | 11/2004 |
| WO | 99/25252 | 5/1999 | | | |
| WO | 99/44510 | 9/1999 | | | |
| WO | 99/44542 | 9/1999 | | | |
| WO | 99/51167 | 10/1999 | | | |
| WO | 99/55236 | 11/1999 | | | |
| WO | 00/07521 | 2/2000 | | | |
| WO | 00/07656 | 2/2000 | | | |
| WO | 00/16705 | 3/2000 | | | |
| WO | 00/21604 | 4/2000 | | | |

OTHER PUBLICATIONS

Rolf W. Gunther et al., "Minibasket for Percutaneous Embolectomy and Filter Protection Against Distal Embolization: Technical Note", Cardiovasular and Interventional Radiology, Springer—Verlag New York Inc. 1991.

US 6,348,062, 02/2002, Hopkins et al. (withdrawn)

* cited by examiner

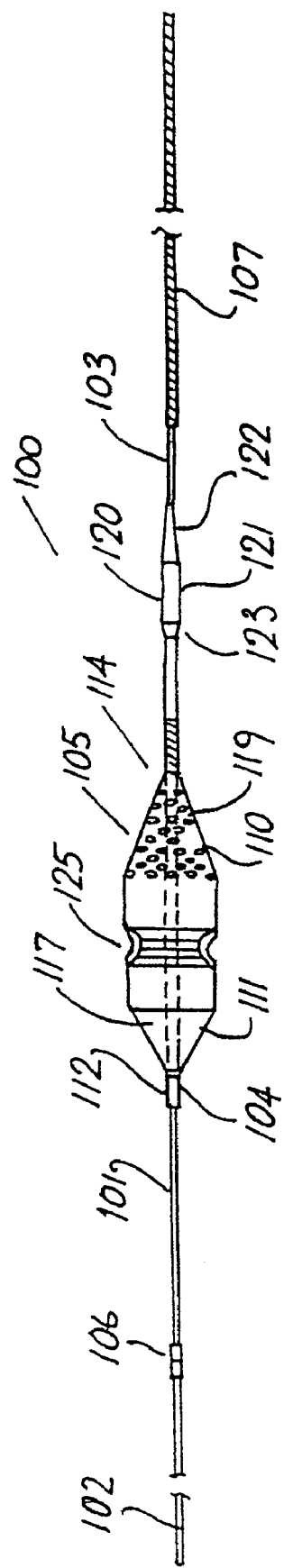

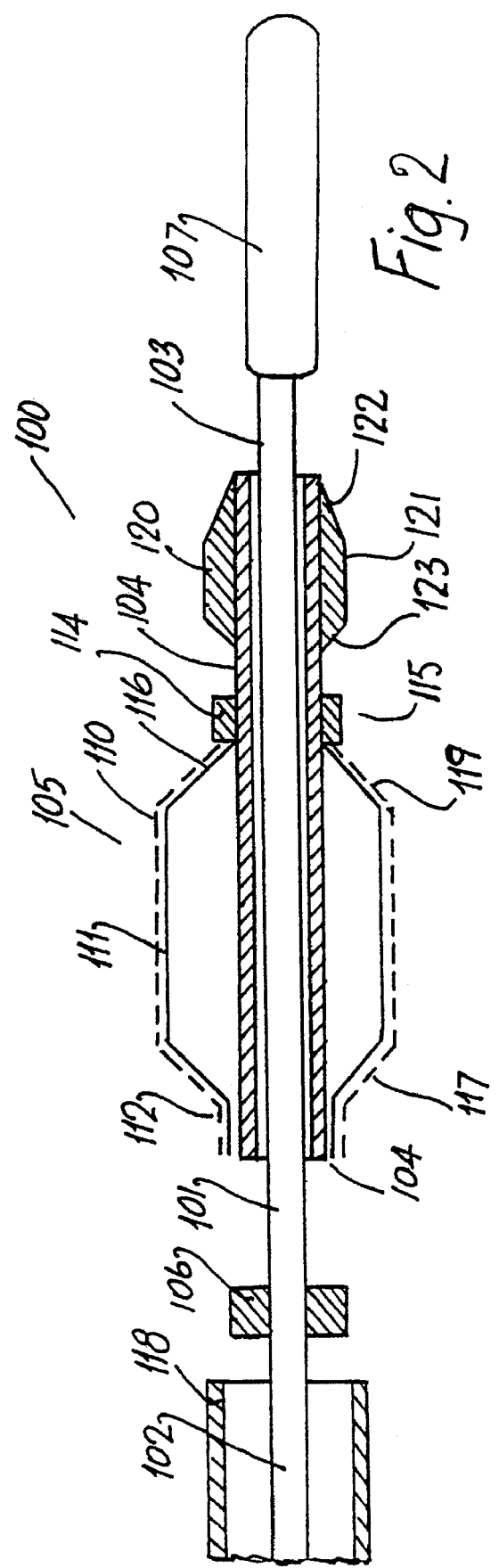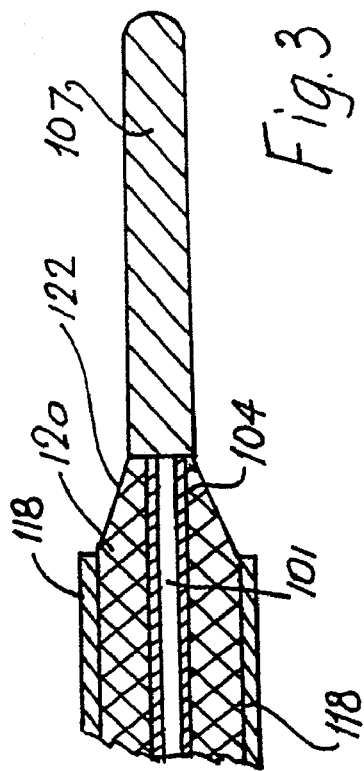

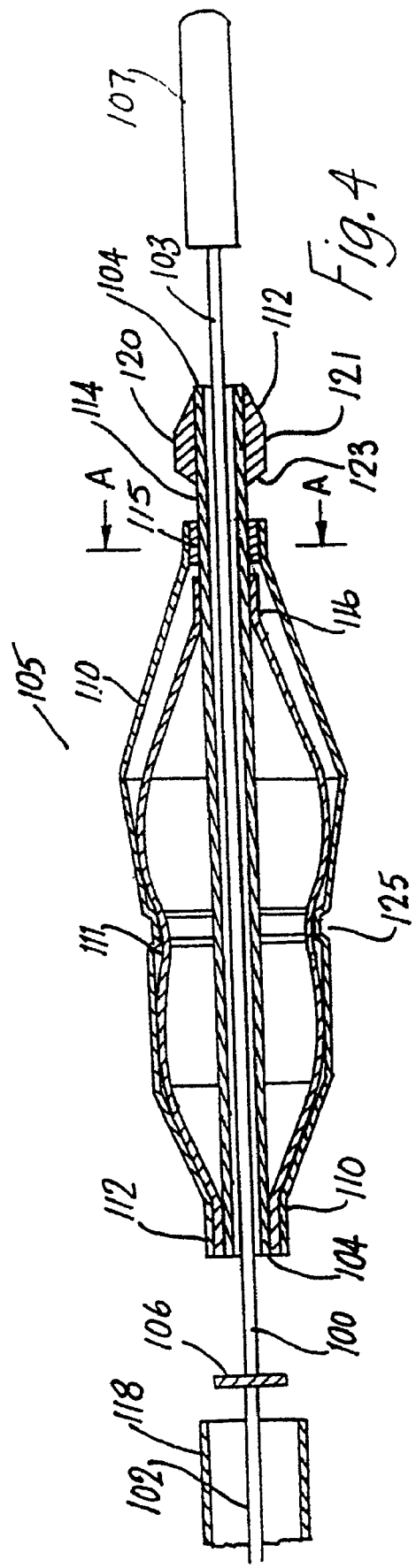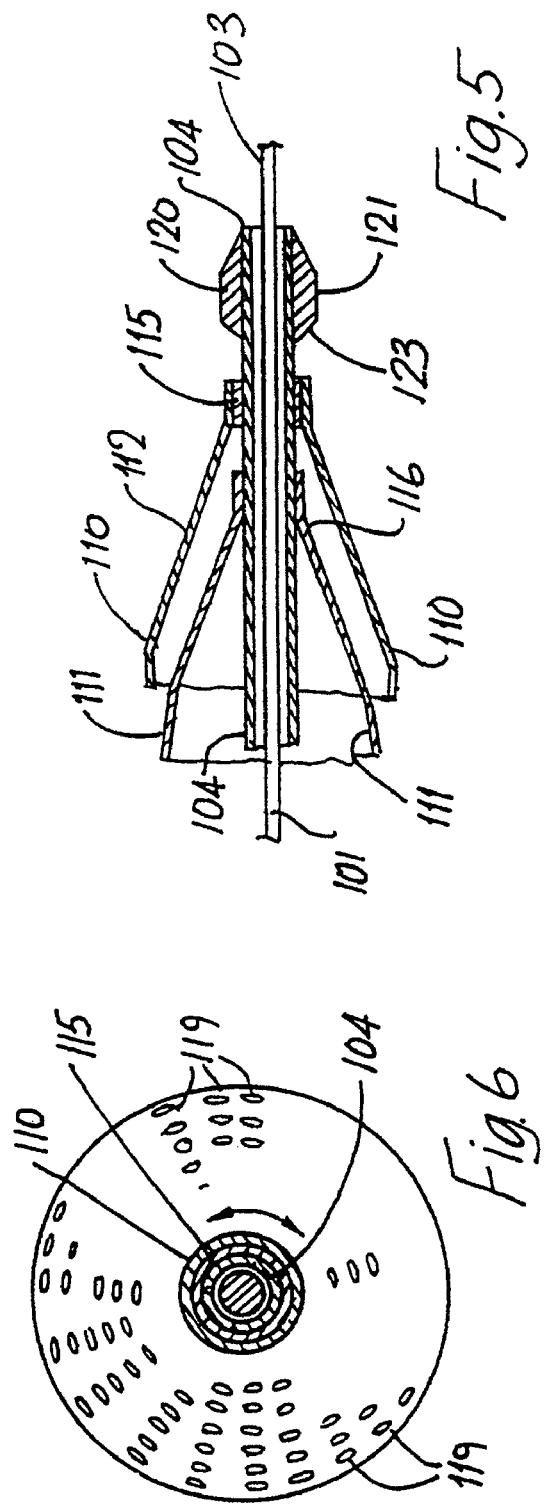

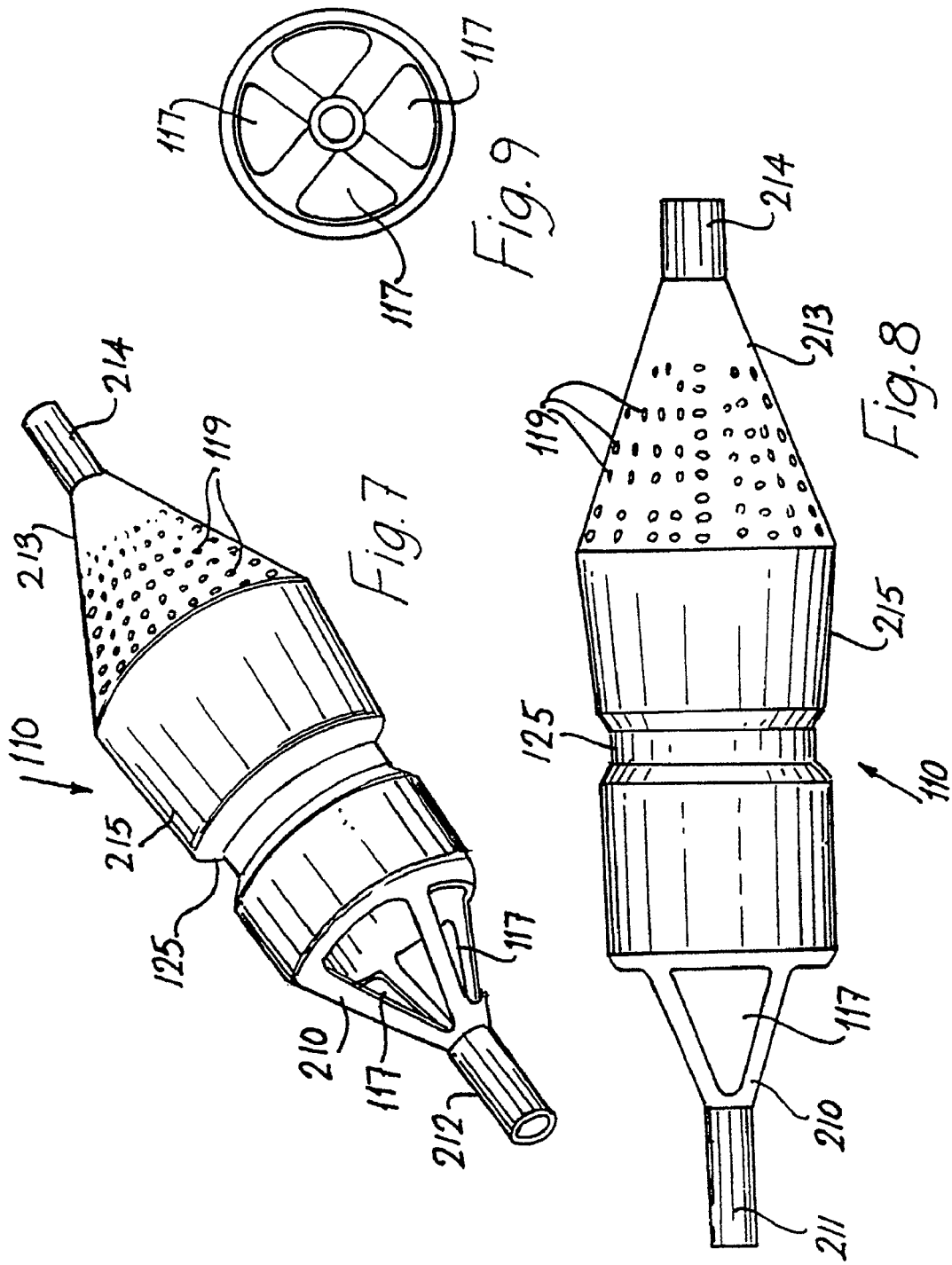

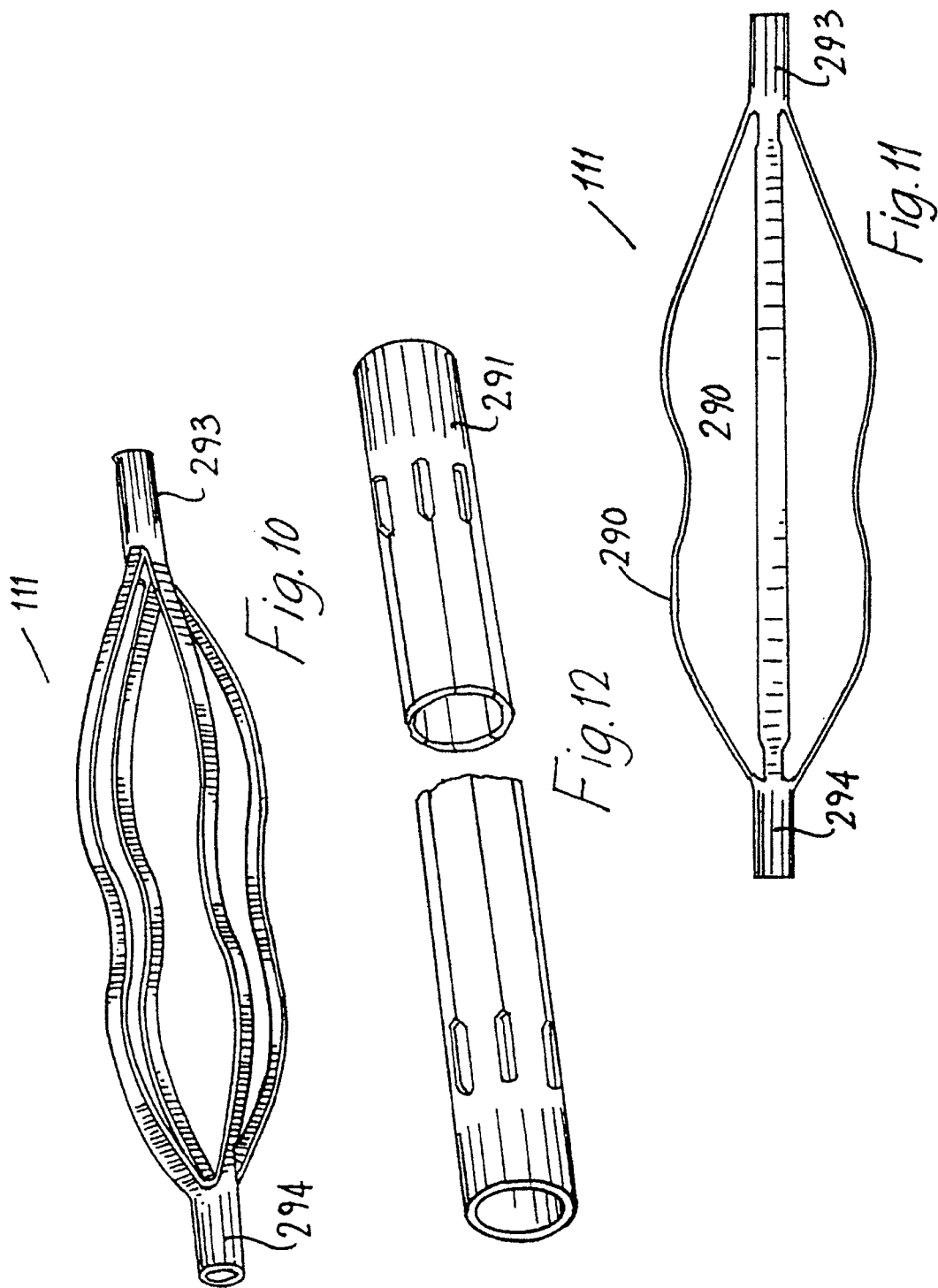

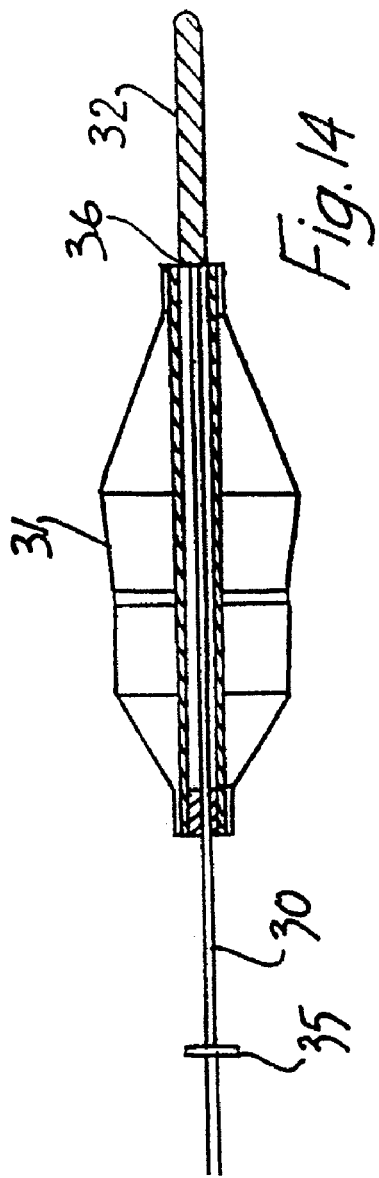
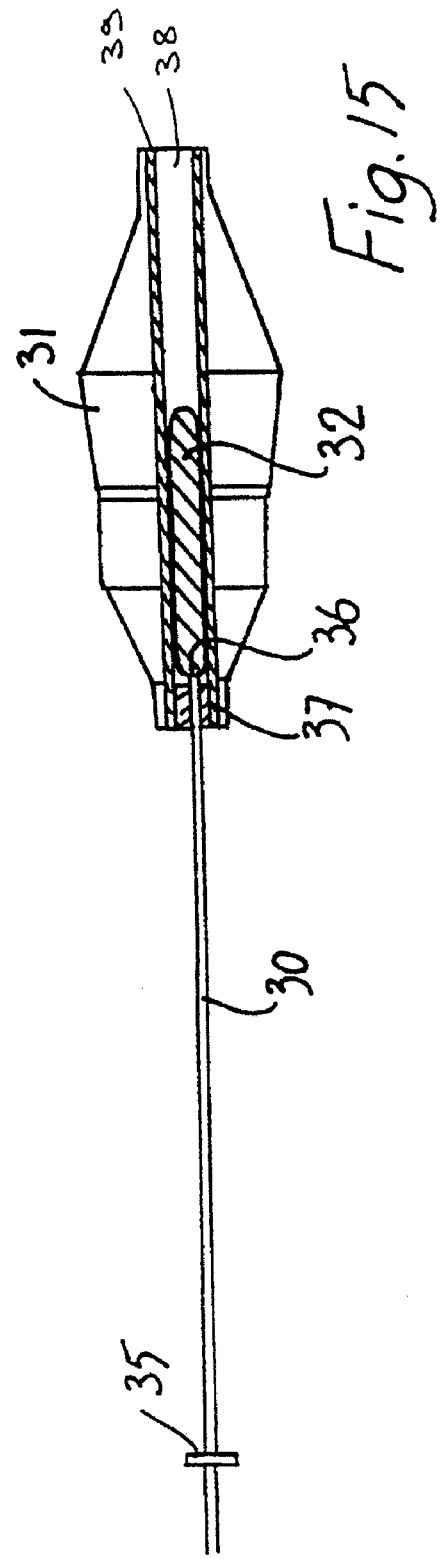

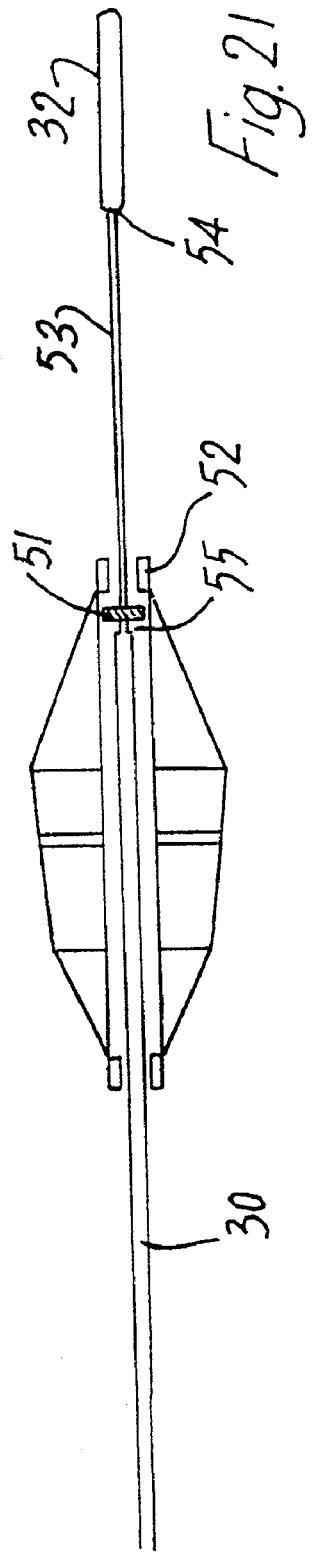
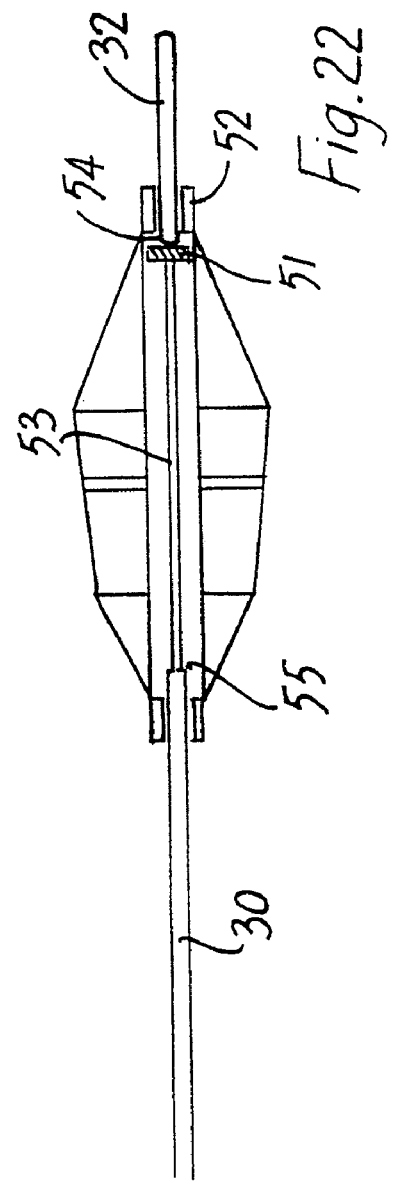
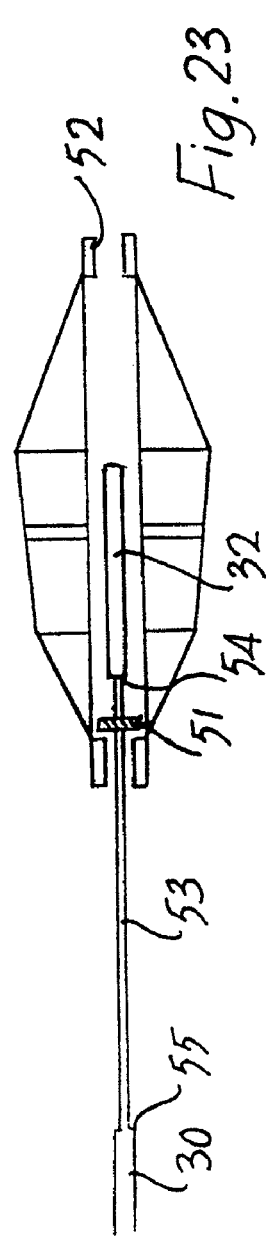

FILTER ELEMENT WITH RETRACTABLE GUIDEWIRE TIP

CROSS REFERENCE TO RELATED APPLICATIONS

This application is a continuation application of U.S. application Ser. No. 12/339,375, filed Dec. 19, 2008, now allowed, which is a divisional application of U.S. application Ser. No. 10/189,375, filed Jul. 3, 2002, now U.S. Pat. No. 7,491,216, which is a continuation of U.S. application Ser. No. 09/986,060, filed Nov. 7, 2001, now abandoned, which is a continuation of PCT/IE00/00057, filed May 8, 2000, and which is a continuation-in-part of U.S. application Ser. No. 09/188,472, filed Nov. 9, 1998, now U.S. Pat. No. 6,336,934. In addition, PCT/IE00/00057 claims priority of PCT/IE99/00039, filed May 7, 1999, and U.S. application Ser. No. 09/188,472, now U.S. Pat. No. 6,336,934, claims priority of Irish Patent Application No. 98/0267 filed Apr. 8, 1998, and Irish Patent Application No. 97/0789 filed Nov. 7, 1997. The contents of each of the above-listed applications are incorporated herein by reference in their entirety.

FIELD OF INVENTION

This invention relates to a filter element for a transcatheter embolic protection device.

INTRODUCTION

The invention is particularly concerned with filter elements for transcatheter embolic protection devices of the type described in our WO-A-9923976. One type of such embolic filter essentially comprises a filter body mounted on an associated collapsible support frame which can be collapsed against the guidewire by means of a catheter for deployment of the filter through a patient's vascular system. Upon retraction of the catheter the support frame and filter body expand outwardly from the guidewire across a blood vessel within which the filter is positioned to filter blood flowing through the blood vessel.

One problem with the filter device is that there is a guidewire tip on the distal end which is required for guiding the filter into a desired position. The guidewire tip needs to be relatively long to provide a smooth tip transition. However, the guidewire distal tip may interfere with the optimal placement of the filter element.

The present invention is directed towards overcoming this problem.

STATEMENTS OF INVENTION

According to the invention there is provide a medical guidewire assembly comprising:
a guidewire having a flexible tip at a distal end of the guidewire;
a medical device mounted near the distal end of the guidewire proximally of the tip, the medical device being movable relative to the tip for adjustment of the amount of the tip extending distally of the medical device;
and means to limit the movement of the medical device relative to the tip.

In a preferred embodiment of the invention the means to limit the movement of the medical device comprise one or more stiff limiting elements.

Preferably at least one limiting element is provided on the guidewire. The limiting element may be fixedly mounted to the guidewire. Alternatively, the limiting element is slidably mounted on the guidewire. In this case preferably the assembly includes stop means to limit slidable movement of the limiting element relative to the guidewire. The stop means to limit slidable movement of the limiting element preferably comprises a pair of stops spaced axially apart along the guidewire. The stops may be provided by abutment surfaces formed in the guidewire.

In a preferred embodiment of the invention at least one limiting element is mounted to the medical device. Preferably the limiting element is mounted to the medical device at the proximal end of the medical device. In one arrangement the limiting element is mounted intermediate proximal and distal ends of the medical device.

In one embodiment of the invention at least one limiting element is stiff relative to the guidewire.

Alternatively or additionally at least one limiting element is compliant relative to the guidewire.

Preferably the medical device and the tip are slidable relative to each other. Ideally, the medical device has a receiver slot for reception of at least portion of the tip. In one embodiment of the invention the tip is fully retractable within the receiver slot.

In a particularly preferred embodiment of the invention the medical device is a collapsible embolic filter mounted on a tubular sleeve which is slidably mounted on the guidewire adjacent the distal end of the guidewire, the sleeve having a bore through which the guidewire passes, said bore forming a receiver slot for reception of the flexible tip of the guidewire which is at least partially retractable within the bore of the sleeve.

Preferably the tip is fully retractable within the bore of the sleeve.

In one embodiment a guidewire limiting element is mounted to the guidewire proximal of the embolic filter and a filter limiting element is mounted to the filter within the bore of the sleeve, the guidewire being movable relative to the filter between the first and second limiting elements. In this case preferably the guidewire has an abutment which is engagable with the filter limiting element when the guidewire tip is retracted. In one embodiment the abutment is provided by a shoulder of the tip.

In one arrangement the filter limiting element is provided at a proximal end of the filter.

In another arrangement the filter limiting element is provided intermediate proximal and distal ends of the filter.

In another embodiment of the invention a guidewire limiting element is mounted to the guidewire intermediate proximal and distal ends of the filter and the filter has a proximal filter limiting element and a distal filter limiting element, the guidewire limiting element being movable with the guidewire between the proximal and distal filter limiting elements.

In one case the guidewire tip is retractable proximally of the distal filter limiting element.

Preferably the guidewire limiting element is movable on the guidewire. In this case the assembly includes stop means to limit slidable movement of the guidewire limiting element relative to the guidewire. The stop means may comprise a pair of stops spaced axially apart along the guidewire. The stops may be provided by abutment surfaces formed in the guidewire. In one embodiment the guidewire has a recessed portion of reduced diameter on which the guidewire limiting element is mounted.

In another aspect the invention provides an embolic protection device comprising:
a collapsible filter element mounted on a filter carrier for delivery through a vascular system of a patient;

the filter element being movable between a collapsed stored position against the filter carrier for movement through the vascular system, and an expanded position for occluding a blood vessel such that blood passing through the blood vessel is delivered through the filter element;

the filter element comprising a collapsible filter body having an inlet end and an outlet end;

the inlet end of the filter body having one or more inlet openings sized to allow blood and embolic material enter the filter body; the outlet end of the filter body having a plurality of outlet openings sized to allow through passage of blood but to retain undesired embolic material within the filter body;

the collapsible filter element being slidably mounted on the filter carrier for axial movement of the filter element along the filter carrier; and means to limit the movement of the filter element relative to the filter carrier, the means being arranged to allow a distal end of the filter carrier to be substantially retracted into the filter element.

In one embodiment of the invention the means to limit the movement of the filter element comprise one or more limiting elements.

At least one limiting element is preferably provided on the filter carrier.

The limiting element may be fixedly mounted on the filter carrier.

Alternatively the limiting element is slidably mounted on the filter carrier. In this case the device preferably includes stop means to limit the movement of the limiting element relative to the filter carrier. The means to limit the movement of the limiting element may comprise a pair of stops spaced axially apart along the filter carrier. The stops may be provided by abutment surfaces formed on the filter carrier.

In a preferred embodiment of the invention at least one limiting element is mounted to the filter element. The limiting element may be mounted to the filter element intermediate the proximal and distal ends of the filter element.

In a further embodiment of the invention the filter element is mounted on a guidewire such that the guidewire has freedom to rotate and/or move axially independently of the filter. More preferably the wire has complete freedom to rotate independently of the filter and has limited axial movement. The limit of axial movement is determined by stops mounted on or connected to the wire. Ideally the wire can move 100 mm in the axial direction independent of the filter. More ideally the wire can move less than 50 mm independently of the filter. This embodiment facilitates the maintenance of filter position during the exchange of catheters and permits the steering of the wire independent of the filter.

In one embodiment of the invention at least one limiting element is stiff relative to the filter carrier. Alternatively or additionally at least one limiting element is compliant relative to the filter carrier.

The limiting element may be mounted to the filter element at the proximal end of the filter element.

In a particularly preferred embodiment of the invention the filter carrier is a guidewire. Preferably the distal end of the guidewire includes a guiding tip which may be substantially retracted into the filter element.

The invention also provides a method for positioning a medical device in a body lumen comprising the steps of:

providing a medical guidewire assembly of the invention;

advancing the assembly into a body lumen with the guidewire tip extending distally of the medical device to a first location;

moving the medical device relative to the tip to advance the medical device to a second location which is distally advanced from the first location.

BRIEF DESCRIPTION OF THE DRAWINGS

The invention will be more clearly understood by the following description of some of the embodiments thereof, given by way of example only, with reference to the accompanying drawings, in which:

FIG. 1 is partially sectioned elevational view of an embolic protection device;

FIG. 2 is a schematic sectional elevational view of the embolic protection device of FIG. 1;

FIG. 3 is a detail sectional view of a portion of the device of FIG. 1;

FIG. 4 is a longitudinal cross sectional view of the device of FIG. 1;

FIG. 5 is a cross sectional view of a distal end of the device of FIG. 1;

FIG. 6 is a view on the line A-A in FIG. 4;

FIG. 7 is a perspective view of a filter body of the device of FIGS. 1 to 6;

FIG. 8 is a side elevational view of the filter body of FIG. 7;

FIG. 9 is a view on a proximal end of the filter body;

FIG. 10 is a perspective view of a support frame of the device of FIGS. 1 to 6;

FIG. 11 is a side elevational view of the support frame;

FIG. 12 is a perspective view illustrating the manufacture of the support frame;

FIG. 14 is a side partially cross sectional view of a filter body and guidewire according to one embodiment of the invention in one position of use;

FIG. 15 is a side view similar to FIG. 14 in another position of use;

FIGS. 21 to 23 are side, partially cross sectional views of a filter body and guidewire according to a further embodiment of the invention in different positions of use.

DETAILED DESCRIPTION

Figure 13:
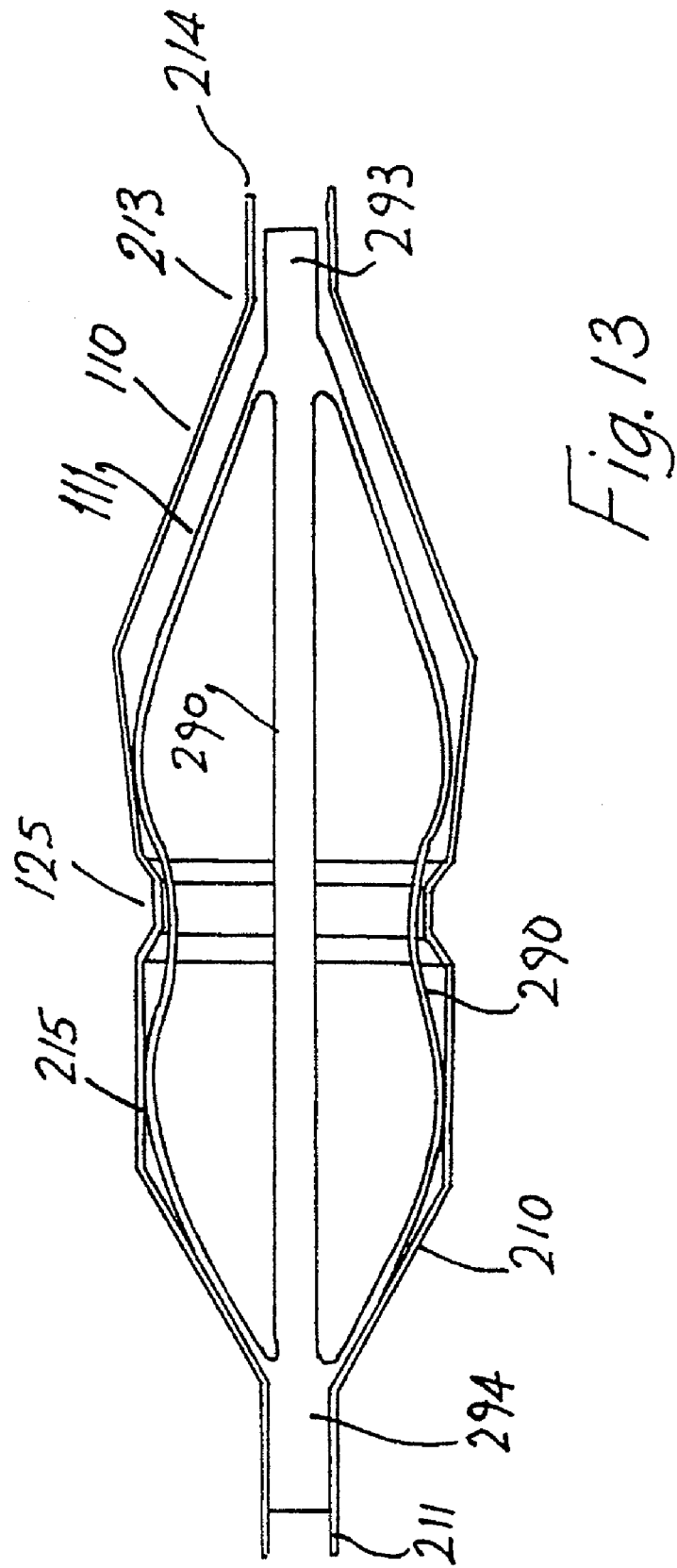
FIG. 13 is a view of the support frame and filter body assembly.

Referring to FIGS. 1 to 13 there is illustrated an embolic protection device as described in our WO-A-9923976 indicated generally by the reference number 100. The device 100 has a guidewire 101 with a proximal end 102 and a distal end 103. A tubular sleeve 104 is slidably mounted on the guidewire 101. A collapsible filter 105 is mounted on the sleeve 104, the filter 105 being movable between a collapsed stored position against the sleeve 104 and an expanded position as shown in the drawings extended outwardly of the sleeve 104 for deployment in a blood vessel.

The sleeve 104 is slidable on the guidewire 101 between a pair of spaced-apart end stops, namely an inner stop 106 and an outer stop which in this case is formed by a spring tip 107 at the distal end 103 of the guidewire 101.

The filter 105 comprises a filter body 110 mounted over a collapsible support frame 111. The filter body 110 is mounted to the sleeve 104 at each end, the body 110 being rigidly attached to a proximal end 112 of the sleeve 104 and the body 110 being attached to a collar 115 which is slidable along a distal end 114 of the sleeve 104. Thus the distal end of the body 110 is longitudinally slidable along the sleeve 104. The support frame 111 is also fixed at the proximal end 112 of the sleeve 104. A distal end 116 of the support frame 111 is not attached to the sleeve 104 and is thus also free to move longitudinally along the sleeve 104 to facilitate collapsing the support frame 111 against the sleeve 104. The support frame 111 is such that it is naturally expanded as shown in the drawings and can be collapsed inwardly against the sleeve 104 for loading in a catheter 118 or the like.

The filter body 105 has large proximal inlet openings 117 and small distal outlet openings 119. The proximal inlet openings 117 allow blood and embolic material to enter the filter body, while, the distal outlet openings 119 allow through passage of blood but retain undesired embolic material within the filter body.

An olive guide 120 is mounted at a distal end of the sleeve 104 and has a cylindrical central portion 121 with tapered ends 122, 123. The distal end 122 may be an arrowhead configuration for smooth transition between the catheter and olive surfaces. The support frame 111 is shaped to provide a circumferential groove 125 in the filter body 110. If the filter is too large for a vessel, the body may crease and this groove 125 ensures any crease does not propagate along the filter.

Enlarged openings are provided at a proximal end of the filter body 110 to allow ingress of blood and embolic material into an interior of the body 110.

In use, the filter 105 is mounted in a collapsed state within a distal end of the catheter 118 and delivered to a deployment site. When the filter is correctly positioned the catheter 118 is retracted allowing the support frame 111 to expand expanding the filter body 110 across the vessel in which the filter is mounted. Blood and emboli can enter the enlarged openings at a proximal end of the filter body 110. The blood will pass through the filter body, however, the openings or pores in the filter body are sized so as to retain the embolic material. After use, a retrieval catheter 18 is delivered along the guidewire 101 and slid over the filter 105 engaging the proximal inlet end 112 first to close the openings and then gradually collapsing the filter body against the sleeve 104 as the catheter 118 advances over the filter 105. Once the filter 105 is fully loaded in the catheter 118, it can then be withdrawn.

It will be noted that a proximal end of the filter is fixed and a distal end of the filter is longitudinally movable along the sleeve to facilitate collapsing of the filter body.

Further, the catheter engages the proximal end of the filter body first thus closing the filter body inlet and preventing escape of embolic material from the filter body as the filter body is being collapsed.

The outer filter body 110 is preferably of a resilient biocompatible elastomeric material. The material may be a polyurethane based material. There are a series of commercially available polyurethane materials that may be suitable. These are typically based on polyether or polycarbonate or silicone macroglycols together with diisocyanate and a diol or diamine or alkanolamine or water chain extender. Examples of these are described in EP-A-461,375 and U.S. Pat. No. 5,621,065. In addition, polyurethane elastomers manufactured from polycarbonate polyols as described in U.S. Pat. No. 5,254,622 (Szycher) are also suitable.

The filter material may also be a biostable polycarbonate urethane article an example of which may be prepared by reaction of an isocyanate, a chain extender and a polycarbonate copolymer polyol of alkyl carbonates. This material is described in our WO-A-9924084. The filter material may be manufactured from a block and cut into a desired shape. However the filter is preferably formed by dipping a rod of desired geometry into a solution of the material which coats the rod. The rod is then dissolved. The final geometry of the filter may be determined in the dipping step or the final geometry may be achieved in a finishing operation. Typically the finishing operations involve processes such as mechanical machining operations, laser machining or chemical machining.

The filter body is of hollow construction and is formed as described above by dipping a rod in a solution of polymeric material to coat the rod. The rod is then dissolved, leaving a hollow body polymeric material. The rod may be of an acrylic material which is dissolved by a suitable solvent such as acetone.

The polymeric body thus formed is machined to the shape illustrated in FIGS. 1 to 13. The final machined filter body comprises an inlet or proximal portion 210 with a proximal neck 212, and outlet or distal portion 213 with a distal neck 214, and an intermediate portion 215 between the proximal and distal portions.

The inlet holes 117 are provided in the proximal portion 210 which allow the blood and embolic material to flow into the filter body. In this case the proximal portion 210 is of generally conical shape to maximize the hole size.

The intermediate portion 215 is also hollow and in this case is of generally cylindrical construction. This is important in ensuring more than simple point contact with the surrounding blood vessel. The cylindrical structure allows the filter body to come into soft contact with the blood vessel to avoid damaging the vessel wall.

The intermediate portion 215 is provided with a radial stiffening means, in this case in the form of a radial strengthening ring or rim 220. The ring 220 provides localized stiffening of the filter body without stiffening the material in contact with the vessel. Such an arrangement provides appropriate structural strength so that line apposition of the filter body to the vessel wall is achieved. It is expected that other geometries of stiffening means will achieve a similar result.

The tubular intermediate portion 215 is also important in maintaining the stability of the filter body in situ to retain captured emboli and to ensure that flow around the filter is minimized. For optimum stability we have found that the ratio of the axial length of the intermediate portion 215 of the filter body to the diameter of the intermediate portion 215 is preferably at least 0.5 and ideally greater than 1.0.

The collapsible support frame 111 has four foldable arms 290 which are collapsed for deployment and upon release extend outwardly to expand the filter body 110.

The support frame 111 can be manufactured from a range of metallic or polymeric components such as a shape memory alloy like nitinol or a shape memory polymer or a shaped stainless steel or metal with similar properties that will recover from the deformation sufficiently to initiate opening of the filter body 110.

The support frame may be formed as illustrated in FIG. 12 by machining slots in a tube 291 of shape memory alloy such as nitinol. On machining, the unslotted distal end of the tube forms a distal collar 293 and the unslotted proximal end of the tube forms a proximal collar 294. In use, the distal collar 293 is slidably moveable along the tubular sleeve 104 which in turn is slidably mounted on the guidewire 101 for deployment and retrieval. The proximal collar 294 is fixed relative to the tubular sleeve 104.

To load the filter the sub assembly of the support frame and filter body is pulled back into the catheter 118 to engage the distal stop 107. The support arms 290 are hinged inwardly and the distal collar 293 moves forward along the tubular sleeve 104. As the support arms 290 enter the catheter 118 the filter body 110 stretches as the filter body collar 115 slides along the tubular sleeve 104 proximal to the olive 120. On deployment, the catheter 118 is retracted proximally along the guidewire 101 initially bringing the collapsed filter assembly with it until it engages the proximal stop 106. The catheter sleeve then begins to pull off the filter, freeing the support arms 290 to initiate opening of the filter body to oppose the vessel wall.

For retrieval, a retrieval catheter is introduced by sliding it over the guidewire 101 until it is positioned at the proximal end of the filter body and support frame. Pulling the guidewire 101 will initially engage the distal stop 107 with the filter element and begin to pull it into the retrieval catheter. The initial travel into the delivery catheter acts to close the proximal openings of the filter element, thus entrapping the embolic load. As the filter continues to be pulled back the filter body and the support frame are enveloped in the retrieval catheter. The collapsed filter may then be removed from the patient.

Referring to FIGS. 14 and 15 there is illustrated a medical guidewire assembly according to one embodiment of the invention. A filter 31 is mounted on a guidewire 30 and projecting from the distal end of the guidewire 30 is a guidewire tip 32. The guidewire tip 32 is slidable in a bore 38 in a sleeve 39 of the filter 31. When the filter 31 is being maneuvered into place the guidewire tip 32 facilitates the maneuvering of the filter device. By advancing and retracting the tip 32 relative to the filter assembly 31 it is possible to maneuver the guidewire tip 32 around various portions of the anatomy, for example, where it is particularly tortuous, or where the guidewire tip 32 has to cross lesions. The tip 32 can be partially retracted to give a stiffer tip, or can be fully retracted in the deployment position, FIG. 15.

The guidewire 30 is slidable between a proximal guidewire limiting element 35 on the guidewire 30 and a filter limiting element 37 provided at a proximal end of the filter 31. A stop defined by a shoulder 36 of the tip 32 is engagable against the limiting element 37.

The proximal limiting element 35 and the filter limiting element 37 are of a relatively stiff material, such that upon engagement of the filter 31 with the proximal limiting element 35, or the shoulder 36 with the filter limiting element 37, the limiting elements 35, 37 do not deform. In this way the movement of the filter 31 relative to the guidewire tip 32 is accurately controlled.

One or both of the limiting elements 35, 37 may be of a compliant material. This feature will assist in ensuring that the flexibility of the filter is not affected by the limiting elements.

Figure 16:
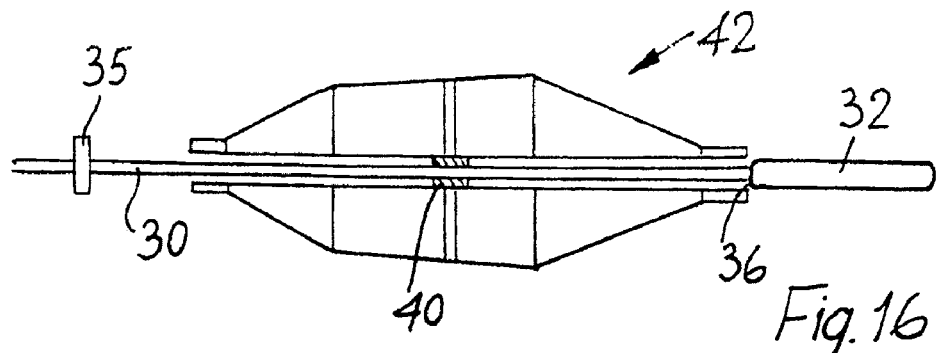
FIG. 16 is a side, partially cross sectional view of a filter body and guidewire according to another embodiment of the invention in one 5 position of use.
Figure 17:
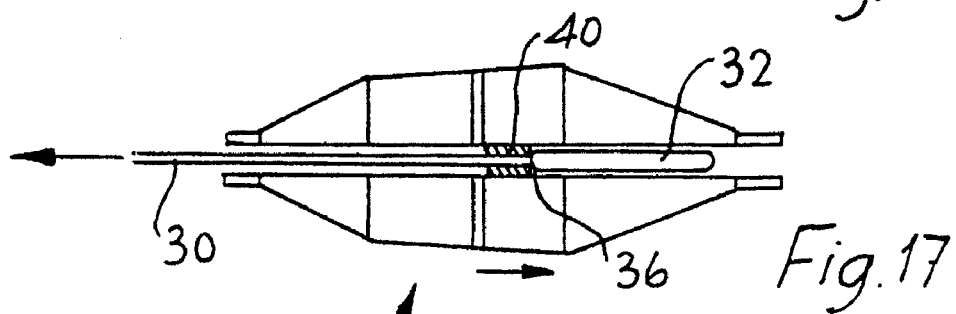
FIG. 17 is a side view similar to FIG. 16 in another position of use.

Referring to FIGS. 16 and 17 there is illustrated a medical guidewire assembly including a filter 42, which is similar to the filter 31 of FIGS. 14 and 15, and the same reference numerals are used to denote similar elements in FIGS. 16 and 17. In this case the guidewire 30 is slidable between a proximal limiting element 35 on the guidewire 30 and a filter limiting element 40 positioned intermediate the proximal and distal ends of the filter 42. A distal stop defined by a shoulder 36 of the tip 32 is engagable against the filter limiting element 40.

Figure 18:
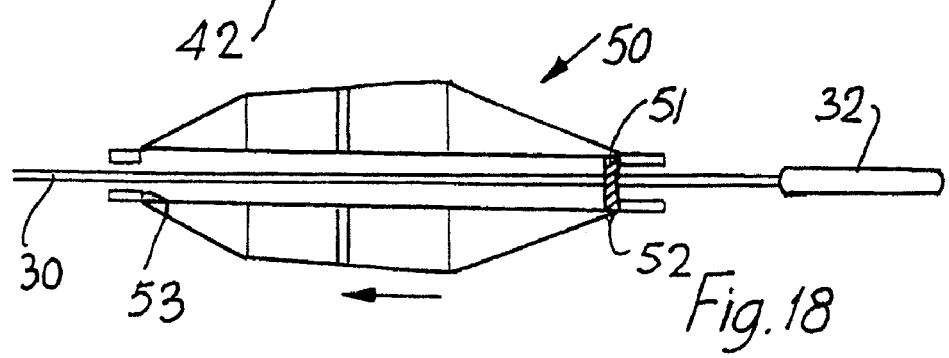
FIG. 18 is a side partially cross sectional view of a filter body and guidewire according to a further embodiment of the invention in one position of use.
Figure 19:
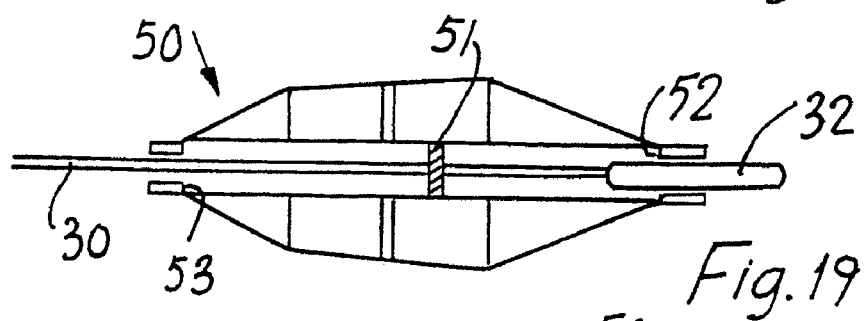
FIGS. 19 and 20 are side views similar to FIG. 18 in other positions of use.
Figure 20:
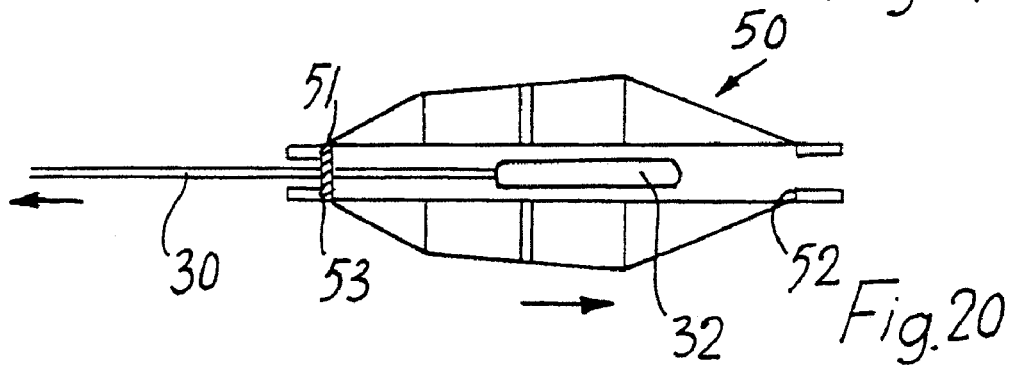

Referring to FIGS. 18 to 20 there is illustrated a medical guidewire assembly 30 including a filter 50, which is similar to filters 31 and 42 of FIGS. 14 to 17, and the same reference numerals are used to denote similar elements in FIGS. 18 to 20. In this arrangement a guidewire limiting element 51 is rigidly fixed to the guidewire 30 proximal of the tip 32, the filter 50 being mounted on the guidewire 30 so that the limiting element 51 is intermediate the proximal and distal ends of the filter 50. The guidewire 30 is slidable between a distal limiting element defined by a proximal shoulder 53 (or mobile attachment point) of the filter 50 which is engagable against the guidewire limiting element 51, and a proximal limiting element defined by a distal shoulder 52 (or mobile attachment point) of the filter 50 which is engagable against the guidewire limiting element 51. In this arrangement there is no obstruction to advancement of another medical device over the guidewire 30 to approach the filter 50 from the proximal direction.

Referring to FIGS. 21 to 23 in an alternative embodiment of the invention, the guidewire limiting element 51 is slidably mounted within a recess 53 provided on the guidewire 30 (i.e., a variable thickness guidewire having a thinner segment between thicker segments), the movement of the limiting element 51 relative to the guidewire 30 being limited between a proximal stop provided by a shoulder 55 of the recess and a distal stop provided by a shoulder 54 provided by the guidewire tip 32. This arrangement provides an even greater degree of freedom for movement of the guidewire 30 relative to the filter.

The filter may be placed over or beyond the distal guidewire tip. Thus, the invention facilitates the optimal placement of a filter device in the limited vasculature space available.

Other medical devices may be advanced over the guidewire to approach the filter from the proximal direction without obstruction. Such devices may be for use in performing angioplasty procedures, stenting and the like. Ready access is also provided to perform emergency procedures such as snaring of a medical device or part, and lysis for treatment of a blood clot.

It will be appreciated that while the invention has been described in relation to an embolic protection device it may also be applied to medial guidewire assemblies for placement of other medical devices.

The invention is not limited to the embodiments hereinbefore described which may be varied in both construction and detail.

The invention claimed is:

1. An embolic protection device for filtering embolic material, debris or clots released during interventional procedures, comprising:
    a variable thickness guidewire comprising a thinner segment bordered by thicker segments; and
    a filtering device movable between an expanded configuration and a collapsed configuration, for deploying beyond an area of blockage or clot in a cerebral arterial blood vessel, the filtering device comprising an expansion assembly, a filter membrane, and a mobile attachment point,
    wherein the filtering device is rotatably mounted on the variable thickness guidewire via the mobile attachment point, such that the filtering device may be rotationally and longitudinally displaced relative to and independently of the guidewire,
    wherein the filtering device allows ingress of blood and embolic material into the interior of the filter body.

2. The embolic protection device of claim 1, wherein the expansion assembly comprises a plurality of struts comprising a biocompatible material, and the filter membrane has a hemispherical, helical or conical shape.

3. The embolic protection device of claim 1, wherein the guidewire comprises a proximal and a distal stop where the thinner segment of the guidewire meets a thicker segment of the guidewire.

4. The embolic protection device of claim 3, wherein the filtering device comprises a distal mobile attachment point, and a proximal mobile attachment point, and the mobile attachment points are rotatably disposable on the thinner segment of the guidewire between the proximal and distal stops, such that there is rotatory as well as longitudinal mobility of the guidewire through, and independently of, the filtering device between the proximal and distal stops.

5. The embolic protection device of claim 1, wherein the mobile attachment points are short and do not cover the entire length of the thinner segment of the guidewire.

6. The embolic protection device of claim 1, wherein the filter membrane comprises a biopolymer having pores large enough to allow blood cells to pass through the filter but small enough to capture debris and clots that are released during percutaneous neurovascular interventional procedures in the cerebral arterial blood vessels.

7. The embolic protection device of claim 6, wherein the pore openings are sized to capture embolic material of a size greater than 100 microns.

8. The embolic protection device of claim 1, wherein the distal portion of the filtering device is covered by the filter membrane, and wherein the filter membrane comprises a biocompatible elastomeric material.

9. The embolic protection device of claim 1, wherein the distal portion of the filtering device is covered by the filter membrane, and wherein the filter membrane comprises a biostable polycarbonate urethane.

10. The embolic protection device of claim 1, wherein the expansion assembly comprises a plurality of struts.

11. The embolic protection device of claim 10, wherein the plurality of struts are made from a shape memory alloy or shape memory polymer.

12. The embolic protection device of claim 10, wherein the plurality of struts are made from nitinol.

13. The embolic protection device of claim 1, wherein the guidewire comprises a spring tip.

14. The embolic protection device of claim 1, further comprising two mobile attachment points on either end of the filtering device, and the axial length of each mobile attachment point is shorter than the axial length of the thinner segment of the guidewire.

15. The embolic protection device of claim 1, wherein the embolic protection device is not inherently attached to a balloon or a stent while filtering embolic material, debris or clots released during percutaneous neurovascular interventional procedures performed in cerebral arterial blood vessels.

16. A method for collecting embolic material, debris or clots released during percutaneous neurovascular interventional procedures specifically performed in the cerebral arterial blood vessels, comprising:
    inserting the embolic protection device of claim 1 into a cerebral arterial blood vessel having an area of stenosis or a clot; and
    deploying the filtering device distal to the area of blockage or clot and allowing the filtering device to expand to fill the diameter of the cerebral arterial blood vessel.

17. The method of claim 16, further comprising:
    advancing a catheter towards the area of stenosis or clot;
    positioning the catheter distal to the area of stenosis or clot; and
    withdrawing the catheter,
    wherein the embolic protection device is advanced to the position distal to the area of stenosis or clot via the catheter.

18. The method of claim 16, wherein a catheter is withdrawn while keeping the guidewire in position distal to the area of stenosis or clot to unsheathe the embolic protection device and allow the device to expand across the vessel; and
    the expanded shape of the filter membrane is a hemispherical, helical or conical shape.

19. The method of claim 16, further comprising:
    performing an angioplasty procedure at area of stenosis or clot; and
    collecting any debris or clots that are dislodged during the balloon angioplasty in the cerebral arterial blood vessels in the filter membrane of the embolic protection device.

20. The method of claim 16, further comprising;
    performing a stenting procedure at the area of stenosis or clot; and
    collecting any debris or clots that are dislodged during the balloon angioplasty in the cerebral arterial blood vessels in the filter membrane of the embolic protection device.

21. The method of claim 16, further comprising:
    recovering the embolic protection device by advancing a catheter over the guidewire; and
    withdrawing the embolic protection device and the catheter.

* * * * *